United States Patent
Seebach et al.

(12) 
(10) Patent No.: US 6,545,147 B1
(45) Date of Patent: Apr. 8, 2003

(54) BLEACHING-ACTIVE METAL COMPLEXES

(75) Inventors: Michael Seebach, Hattersheim (DE); Gerd Reinhardt, Kelkheim (DE); Thomas Schönherr, Hohenstein-Ernstthal (DE); Edwin Weber, Freiberg (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/658,831

(22) Filed: Sep. 8, 2000

(30) Foreign Application Priority Data

Sep. 10, 1999 (DE) .......................... 199 43 254

(51) Int. Cl.$^7$ ....................... C07D 255/02; C11D 3/395; C07F 13/00

(52) U.S. Cl. ................. 540/465; 510/218; 510/311; 510/372; 510/376; 252/186.33; 544/4; 544/64; 544/181; 544/225; 546/2; 548/402; 548/101; 548/108; 548/955; 549/3; 549/206; 549/208

(58) Field of Search ............... 540/465; 544/4, 544/64, 181, 225; 546/2; 548/101, 108, 402, 955; 549/3, 206, 208; 510/218, 311, 372, 376; 252/186.33

(56) References Cited

U.S. PATENT DOCUMENTS

| | | | |
|---|---|---|---|
| 3,929,678 A | 12/1975 | Laughlin et al. | 252/526 |
| 3,931,037 A | 1/1976 | Hall | 252/135 |
| 4,087,369 A | 5/1978 | Wevers | 252/102 |
| 4,144,226 A | 3/1979 | Crutchfield et al. | 528/231 |
| 4,146,495 A | 3/1979 | Crutchfield et al. | 252/89 R |
| 4,271,030 A | 6/1981 | Brierley et al. | 252/98 |
| 4,583,217 A | 4/1986 | Kittel | 370/29 |
| 4,715,979 A | 12/1987 | Moore | 252/91 |
| 4,965,015 A | 10/1990 | Heybourne et al. | 252/174.25 |
| 5,284,944 A * | 2/1994 | Madison et al. | 540/474 |
| 5,654,265 A | 8/1997 | Kuroda et al. | 510/507 |
| 5,898,025 A * | 4/1999 | Burg et al. | 510/229 |
| 6,075,001 A | 6/2000 | Wilde | 510/376 |
| 6,153,576 A | 11/2000 | Blum et al. | 510/311 |
| 6,225,274 B1 | 5/2001 | Nitsch et al. | 510/314 |
| 6,302,921 B1 * | 10/2001 | Delroisse et al. | 8/111 |

FOREIGN PATENT DOCUMENTS

| | | |
|---|---|---|
| CA | 1102966 | 6/1981 |
| DE | 26 26 383 | 12/1977 |
| DE | 195 29 905 | 2/1997 |
| DE | 196 05 688 | 8/1997 |
| DE | 196 16 693 | 11/1997 |
| DE | 196 16 767 | 11/1997 |
| DE | 196 49 375 | 6/1998 |
| EP | 0 062 523 | 10/1982 |
| EP | 0 101 634 | 2/1984 |
| EP | 0 240 057 | 10/1987 |
| EP | 0 241 962 | 10/1987 |
| EP | 0 336 635 | 10/1989 |
| EP | 0 458 397 | 11/1991 |
| EP | 0 525 239 | 2/1993 |
| EP | 0 737 739 | 10/1996 |
| EP | 1083173 A2 * | 3/2001 ......... C07D/255/02 |
| EP | 1113068 A2 * | 7/2001 ............ C11D/3/12 |
| EP | 1113068 A9 * | 12/2001 ........... C11D/3/12 |
| GB | 1 561 333 | 2/1980 |
| GB | 2 199 338 | 7/1988 |
| WO | WO 96/06154 | 2/1996 |
| WO | 00/27980 | 5/2000 |
| WO | 00/58435 | 10/2000 |

OTHER PUBLICATIONS

J. Am. Chem. Soc. 1989, 111, 5102–5112, Simulation Strategies for Unusual EPR Spectra of Binuclear Mixed–Valence Manganese Complexes: Synthesis, Properties, and X–ray Structures of the MnII and MnIII complexes.

J. Am. Chem. Soc. 1994, 116, 10334–10335, Synthesis of the Unsymmetrical Dinucleating Ligand that Leads to an Asymmetric Dicopper(II) Complex Having Different Donor Sets at Each Copper.

EPO Search Report for Application No. 00126667, mail date Nov. 5, 2001.

English abstract for DE 2626383, Dec. 22, 1977.
English abstract for DE 19529905, Feb. 20, 1997.
English abstract for DE 19616767, Nov. 6, 1997.
English abstract for WO 00/58435, Oct. 5, 2000.

Basil A Eldadah, et al., The Journal of Neuroscience, Jan. 1, 2000, 20(1) "Ribozyme–Mediated Inhibition of Caspase–3 Protects Cerebellar Granule Cells from Apoptosis Induced by Serum–Potassium Deprivation" p. 179–186, XP–002176296.

English abstract for JP 61–069900.

* cited by examiner

*Primary Examiner*—Porfirio Nazario-Gonzalez
(74) *Attorney, Agent, or Firm*—Richard P. Silverman

(57) ABSTRACT

Compounds of the formula I $$[L_n M_m X_p]^z Y_q \quad (1)$$

are claimed, where L is a ligand of the formula II $$(II)$$

and the individual symbols have the meanings defined in the description. The metal complexes are suitable as bleaching catalysts in detergents, cleaners and disinfectants which comprise peroxy compounds.

8 Claims, No Drawings

BLEACHING-ACTIVE METAL COMPLEXES

BACKGROUND OF THE INVENTION

It is known that the bleaching power of peroxide bleaches, such as hydrogen peroxide, perborates, percarbonates, persilicates and perphosphates, in detergents and cleaners, and hence their efficiency in removing tea, coffee, fruit or red wine stains, is only fully attained at temperatures of significantly greater than 60° C. To improve the bleaching effect, which is greatly reduced at, especially, temperatures below 60° C., it is possible to use compounds to activate the peroxide bleaches. A number of transition metal salts or corresponding complexes with mostly chelating compounds have been proposed for this purpose, although the effectiveness of a metal or of a specific combination of transition metal and complex ligand cannot be predicted.

WO 96 06154 and EP 458 397 claim metal complexes with a high activation potential. A disadvantage of the types of complex described therein is that they considerably damage the fibers and colors of textiles. J. Am. Chem. Soc., 1989, 111, 5102–5114 describes the crystalline structure of a bicyclic manganese complex containing a bridging 2,6-bis(1,4,7-triazacyclononan-1-ylmethyl)4-methylphenoxide ligand, two bridging acetate groups and two perchlorate anions, where the oxidation states of the two metal centers are mixed, and one manganese atom is ascribed the oxidation number II and the second manganese atom the oxidation number III. The applications-related relevance of this compound has hitherto not been reported.

DESCRIPTION OF THE PREFERRED EMBODIMENTS

The present invention therefore provides unknown compounds of the formula I which intensify the bleaching power of peroxo compounds, even at low temperatures, without attacking the textile fibers or textile dyes $$[L_n M_m X_p]^z Y_q \quad \text{formula I}$$

where

M is manganese in oxidation state II, III, IV and/or V, iron in oxidation state II and/or III or cobalt in oxidation state II and/or III, X is a coordination group or bridging group, Y is a counterion in the corresponding stoichiometric amount to balance an existing charge z, where z as the charge of the metal complex can be positive, zero or negative, n and m, independently of one another, are integers from 1 to 4, p is an integer from 0 to 15, q is z/charge of Y, L is an organic ligand of the general formula II

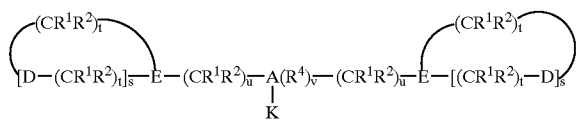

where $R^1$ and $R^2$, independently of one another, are hydrogen, an alkyl group having 1 to 6 carbon atoms, an alkoxy group having 1 to 3 carbon atoms, an alkenyl or alkinyl group having 2 to 8 carbon atoms, a cycloalkyl group having 3 to 10 carbon atoms or a phenyl group which may also be substituted, each D, independently of one another, is $NR^3$, O, $PR^3$ or S, where $R^3$ is an alkyl group having 1 to 6 carbon atoms, an alkenyl or alkinyl group having 2 to 8 carbon atoms, a cycloalkyl group having 3 to 10 carbon atoms or a phenyl group which may also be substituted, each E, independently of one another, is N, P or $C(R^1)$ with the meanings given above for $R^1$, t is a number from 0 to 6, s is a number from 1 to 5 and u is a number from 1 to 4, A is a $C_3$- to $C_8$-cycloalkyl, phenyl, 1,1'-biphenyl, naphthyl, anthracenyl or pyridinyl radical, each $R^4$, independently of one another, is hydrogen, a $C_1$- to $C_6$-alkyl group, a $C_1$- to $C_3$-alkoxy group, a $C_3$- to $C_{10}$-cycloalkyl group or a phenyl group which may also be substituted, v is a number from 0 to 15, K is a group coordinating to at least one of the metal centers M and is of the type —O, —OR, —S, —SR, —$NR_2$, —NR, —$PR_2$ or —PR, where R is hydrogen, an alkyl group having 1 to 6 carbon atoms, an alkenyl or alkinyl group having 2 to 8 carbon atoms, a cycloalkyl group having 3 to 10 carbon atoms or a phenyl group which may also be substituted, X is an anion of the following formulae:

$F^-$, $Cl^-$, $Br^-$, $SCN^-$, $OH^-$, $O_2^{2-}$, $O^{2-}$, $O_2^-$, $R^{10}OO^{31}$, $H_2O$, $HS^{31}$, $CN^-$, $OCN^-$, $S^{2-}$, $N_3^-$, $NH_3$, $NR^{10}_3$, $NR^{10}_2$, $R^{10}O^-$, $R^{10}COO^-$, $R^{10}SO_3^-$ and $R^{10}SO_4^{31}$, where $R^{10}$ is in each case hydrogen, $C_1$- to $C_8$-alkyl, $C_3$- to $C_8$-cycloalkyl or $C_6$- to $C_{18}$-aryl, and

Y if z is positive, is an anion of the following formulae: $F^-$, $Cl^-$, $Br^-$, $NO_3^-$, $ClO_4^-$, $SCN^-$, $PF_6^-$, $R^{10}SO_4^-$, $R^{10}COO^-$, $R^{10}SO_3^-$, $BF_4^-$, $BPh_4^-$ and $SO_4^{2-}$ and if z is negative, is a cation of the following formulae: $Li^+$, $Na^+$, $K^+$, $Mg^{2+}$, $Ca^{2+}$, $Al^{3+}$, $NH_4^+$, $R^{10}NH_3^{30}$, $R^{10}_2NH_2^+$, $R^{10}_3NH^+$ and $R^{10}_4N^+$, where $R^{10}$ has the meaning given above.

Preference is given to compounds in which D is $NR^3$, E is nitrogen, $R^1$ and $R^2$ are hydrogen, s is a number from 1 to 3, t is a number from 1 to 4 and K is a group of the type —O, —OR, —S or —$NR_2$, and the other symbols have the meanings given above.

Particular preference is given to compounds in which A is a phenyl or $C_3$- $C_9$-cycloalkyl group, m is a number from 1 to 3 and n is a number from 1 to 2. If individual symbols in the formula II are a substituted phenyl group, such phenyl groups can be substituted by one to three groups of the following type: $C_1$- $C_4$-alkyl, $C_1$-$C_4$-alkoxy, halogen atoms, substituted or unsubstituted amino or ammonium groups, sulfo groups, carboxyl groups or groups of the formula —$(CH_2)_r$-COOH, —$(CH_2)_r$-$SO_3H$, —$(CH_2)_r$-$PO_3H_2$, —$(CH_2)_l$—OH, where r is an integer from 0 to 4 and l is an integer from 1 to 4, and said acid groups can also be in salt form.

The novel transition metal complexes according to formula I are synthesized from a heterocyclic bridging ligand L according to formula II, e.g. 2,6-bis(4,7-dimethyl-1,4,7-triazacyclonon-1-ylmethyl)-4-methylphenol, dissolved in a polar solvent, for example an alcohol, to which, in the molar ratio 1:2, a transition metal compound, e.g. manganese(II) acetate tetrahydrate, and the required amount of a compound comprising the counterion Y, e.g. $KPF_6$, is added at a pH between 7 and 11 in a temperature range between 0 to 100° C., preferably 25 to 50° C. The bridging ligands of the formula II present in the complexes according to the invention can, for example, be synthesized analogously to the synthesis described in J. Am. Chem. Soc. 1994, 116, 22, 10334–10335, by reacting a heterocyclic compound of the type of the formula III

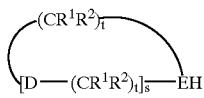
(III)

having the abovementioned definitions for D, E, $R^1$, $R^2$, t and s, for example 1,4-dimethyl-1,4,7-triazacyclononane, dissolved in a polar solvent, preferably an alcohol, in the presence of equimolar amounts of a base, preferably triethylamine, with a compound of the type $Z$-$(CR^1CR^2)_u$-$A(K)(R^4)_v$-$(CR^1CR^2)_U$-$Z$ with the abovementioned definitions for $R^1$, $R^2$, $R^4$, A, K, u and v, where Z is chlorine, bromine, iodine or another leaving group, in the molar ratio 2 to 1 in the temperature range from −30 to 80° C., preferably −10 to 50° C., in the course of 10 to 120 hours.

The novel polycyclic complexes of the formula I are highly suitable as bleaching and oxidation catalysts, in particular in detergents and cleaners, and in the bleaching of textiles and paper. Particular emphasis should be placed here on textile detergents in the form of pulverulent detergents or as liquid formulations, and dishwashing detergents. An advantage of the bleaching catalysts according to the invention is their stability to hydrolysis and oxidation and also their catalytic effect even at low temperatures. In such formulations, they not only improve the bleaching action of hydrogen peroxide, but also of organic and inorganic peroxy compounds.

The present invention accordingly also provides a method of bleaching soiled substrates in which the soiled substrate is brought into contact in an aqueous bleaching liquor with a peroxy compound and an effective amount of one or more of the novel metal complexes according to formula I, where $R^3$ can also be hydrogen and A can also be carbon, as bleaching catalysts.

The detergent and cleaner formulations according to the invention comprise metal complexes of this type in amounts by weight of from 0.0001 to 0.5% by weight of metal, in particular 0.00025 to 0.25% by weight of metal, especially 0.0005 to 0.1% by weight of metal, based on the weight of the formulations.

These detergents and cleaners, which can be in the form of pulverulent or tablet-shaped solids, homogeneous solutions or suspensions, can, in principle, apart from the bleaching catalyst used according to the invention, comprise all known ingredients customary in such compositions, such as peroxygen compounds, bleach activators, further conventional bleaching catalysts, surfactants, builders, water-miscible organic solvents, enzymes, sequestering agents, electrolytes, pH regulators and further auxiliaries, such as silver corrosion inhibitors, foam regulators, thickeners, preservatives, pearlizing agents and emulsifiers, and dyes and fragrances.

Suitable peroxygen compounds are, in particular, organic peracids or salts of organic peracids. Examples thereof are peroxynaphthoic acid, peroxylauric acid, peroxystearic acid, N,N-phthaloylamidoperoxycaproic acid, perbenzoic acid, 1,1 2-diperoxydodecanedioic acid, 1,9-diperoxyazelaic acid, diperoxysebacic acid, diperoxyisophthalic acid, 2-decyldiperoxybutane-1,4-dioic acid, 4,4'-sulfonylbisperoxybenzoic acid and alkanoylamidoperoxycarboxylic acids. Also suitable are hydrogen peroxide and compounds which release hydrogen peroxide and at the washing and cleaning conditions, such as alkali metal peroxides, organic peroxides, such as urea/hydrogen peroxide adducts and inorganic persalts, such as the alkali metal perborates, percarbonates, perphosphates, persilicates, persulfates, peroxynitrites and hydrogen peroxocarbonate peroxohydrates. Particular preference is given to sodium perborate tetrahydrate and, in particular, sodium perborate monohydrate. Sodium perborate monohydrate is preferred because of its good storage stability and its good solubility in water. Sodium percarbonate may be preferred for environmental protection reasons. Alkyl hydroperoxides are a further suitable group of peroxide compounds. Examples of these substance are cumine hydroperoxide and butyl hydroperoxide. Also suitable as peroxy compounds are inorganic peroxi acid salts, e.g. potassium monopersulfate. Mixtures of two or more of these compounds are likewise suitable.

The detergent and cleaner formulations according to the invention usually comprise 1 to 30% by weight, in particular 2 to 25% by weight, of peroxy compounds.

The addition of small amounts of known bleach stabilizers, such as, for example, phosphonates, borates, metaborates and metasilicates and magnesium salts, such as magnesium sulfate, may be expedient.

In addition to the peroxy compounds, the detergents and cleaners can additionally also comprise bleach activators in customary amounts of from about 1 to 10% by weight.

Bleach activators which may be used are compounds which, under perhydrolysis conditions, produce aliphatic percarboxylic acids having, preferably, 1 to 10 carbon atoms, in particular 2 to 4 carbon atoms and/or optionally substituted perbenzoic acid. Suitable substances are those which carry O- and/or N-acyl groups of said number of carbon atoms and/or optionally substituted benzoyl groups. Preference is given to polyacylated alkylenediamine, in particular tetraacetylethylenediamine (TAED), acylated triazine derivates, in particular 1,5-diacetyl-2,4-dioxohexahydro-1,3,5-triazine (DADHT), acylated glycoluriles, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), alkanoylamidocarboxylic esters, in particular alkanoylamidocaproic phenolsulfonates, carboxylic anhydrides, in particular phthalic anhydride, acylated polyhydric alcohols, in particular triacetin, ethylene glycol diacetate, 2,5-diacetoxy-2,5-dihydrofuran, sodium nonanoyloxybenzenesulfonate, sodium isononanoyloxybenzenesulfonate, sodium 4-benzoyloxybenzenesulfonate, sodium trimethylhexanoyloxybenzenesulfonate, lactones, acylals, carboxamides, acyllactams, acylated ureas and oxamides, N-acylated hydantoins, for example 1-phenyl-3-acetylhydantoin, hydrazides, triazoles, hydrotriazines, urazoles, diketopiperazides, sulfurylamides and/or N-acylated lactams, for example N-benzoylcaprolactam, but also quaternary nitrile compounds, for example quaternary trialkylammonium nitrile salts, in particular the cyanomethyltrimethylammonium salt, but also heterocyclically substituted quaternary nitrile compounds and the enol esters known from German Patent Applications DE 196 16 693 and DE 196 16 767, and acylated sorbitol and mannitol or the mixtures thereof described in EP 0 525 239 (SORMAN), acylated sugar derivatives, in particular pentaacetylglucose (PAG), pentaacetylfructose, tetraacetylxylose and octaacetyllactose, and acetylated, optionally N-alkylated glucamine and gluconolactone.

Such bleach activators are present in the customary quantitative range, for example in amounts of from 1 to 10% by weight, in particular 2 to 8% by weight, based on the total composition.

In addition to the conventional bleach activators listed above, or instead of them, it is also possible for sulfonimines and/or further bleach-enhancing transition metal salts or transition metal complexes to be present. Suitable transition metal compounds include, in particular, the manganese, iron, cobalt, ruthenium or molybdenum complexes known from DE 195 29 905 and DE 196 05 688.

As surface-active agents, the detergents and cleaners according to the invention can comprise anionic surfactants in amounts of from approximately 1 to 50% by weight, based on the total amount of all surfactants. Preferred anionic surfactants are $C_8$-$C_{20}$-fatty acid alpha-methyl ester sulfonates, alkyl ether sulfates and secondary alkanesulfonates. The alkyl ether sulfates used in the compositions according to the invention are water-soluble salts or acids of the formula $RO(A)_mSO_3M$, in which R is an unsubstituted $C_{10}$-$C_{24}$-alkyl or $C_{10}$-$C_{24}$-hydroxyalkyl radical, preferably a $C_{12}$-$C_{20}$-alkyl or $C_{12}$-$C_{20}$-hydroxyalkyl radical, particularly preferably $C_{12}$-$C_{18}$-alkyl or $C_{12}$-$C_{18}$-hydroxyalkyl radical. "A" is an ethoxy or propoxy unit, m is a number greater than 0, preferably between 0.5 and about 6, particularly preferably between about 0.5 and about 3, and M is a hydrogen atom or a cation, such as, for example, a metal cation (e.g. sodium, potassium, lithium, calcium, magnesium, etc.), ammonium or a substituted ammonium cation. Specific examples of substituted ammonium cations are methyl, dimethyl, trimethylammonium and quaternary ammonium cations, such as tetramethylammonium and dimethylpiperidinium cations, and those derived from alkylamines, such as ethylamine, diethylamine, triethylamine. Examples of these alkyl ether sulfates which may be mentioned are $C_{12}$-$C_{18}$-alkyl polyethoxylate(1.0) sulfate, ($C_{12}$-$C_{18}$E(1.0)M), $C_{12}$-$C_{18}$-alkyl polyethoxylate(2.25) sulfate ($C_{12}$-$C_{18}$E(2.25)M), $C_{12}$-$C_{18}$-alkyl polyethoxylate(3.0) sulfate ($C_{12}$-$C_{18}$E(3.0)M), $C_{12}$-$C_{18}$-alkyl polyethoxylate(4.0) sulfate ($C_{12}$-$C_{18}$E(4.0)M).

In the case of the secondary alkanesulfonates, the alkyl group can either be saturated or unsaturated, branched or linear and optionally substituted by a hydroxyl group. The sulfo group is randomly distributed over the entire carbon chain, where the primary methyl groups on the start of the chain and on the end of the chain do not have sulfonate groups. Preferred secondary alkanesulfonates contain linear alkyl chains having 9 to 25 carbon atoms, preferably from 10 to 20 carbon atoms and particularly preferably 13 to 17 carbon atoms. The cation is sodium, potassium, ammonium, mono-, di- or triethanolammonium, calcium or magnesium and mixtures thereof. For the sake of simplicity, sodium is preferred as cation.

In addition to or instead of these preferred anionic surfactants, the formulations according to the invention can also comprise other types of anionic surfactants within the limits given above, such as, for example, alkylsulfates, alkylsulfonates, alkylcarboxylates, alkylphosphates and mixtures of said compounds. Suitable cations are, for example, sodium, potassium, calcium or magnesium, and ammonium, substituted ammonium compounds, including mono-, di- or triethanolammonium cations, and mixtures of these cations. The anionic surfactants which are suitable for the present invention have surfactant properties and are water-soluble or water-dispersible.

Here, alkylsulfates are water-soluble salts or acids of the formula $ROSO_3M$, in which R is preferably a $C_{10}$-$C_{24}$-hydrocarbon radical, preferably an alkyl or hydroxyalkyl radical having $C_{10}$-$C_{20}$-alkyl components, particularly preferably a $C_{12}$-$C_{18}$-alkyl or hydroxyalkyl radical. M is hydrogen or a cation, e.g. sodium, potassium, lithium or ammonium or substituted ammonium, e.g. methyl-, dimethyl- and trimethylammonium cations and quaternary ammonium cations, such as tetramethylammonium and dimethylpiperidinium cations and quaternary ammonium cations derived from alkylamines, such as ethylamine, diethylamine, triethylamine and mixtures thereof.

A further suitable anionic surfactant is alkylbenzenesulfonate. The alkyl group can either be saturated or unsaturated, branched or linear and optionally substituted by a hydroxyl group. The preferred alkylbenzenesulfonates contain linear alkyl chains having 9 to 25 carbon atoms, preferably 10 to 13 carbon atoms, and the cation is sodium, potassium, ammonium, mono-, di- or triethylammonium, calcium or magnesium and mixtures thereof.

Further suitable anionic surfactants are carboxylates, e.g. fatty acid soaps and comparable surfactants. The soaps can be saturated or unsaturated and can contain various substituents, such as hydroxyl groups or alpha-sulfonate groups. Preference is given to linear saturated or unsaturated hydrocarbon radicals as hydrophobic component in the soaps. The hydrophobic components usually contain 6 to 30 carbon atoms, preferably 10 to 18 carbon atoms. Further anionic surfactants are salts of acylaminocarboxylic acids, which are formed by reacting fatty acid chlorides with sodium sarcosinate in alkaline medium (acyl sarcosinates), and also fatty acid protein condensation products which are obtained by reacting fatty acid chlorides with oligopeptides. The salts of alkylsulfamidocarboxylic acids and the salts of alkyl and alkylaryl ether carboxylic acids also have surfactant character.

Other anionic surfactants which are useful for use in cleaners are $C_8$-$C_{24}$ olefinsulfonates, sulfonated polycarboxylic acids prepared by sulfonating the pyrolysis products of alkaline earth metal citrates, as described, for example, in GB 1 082 179, alkyl glycerol sulfates, fatty acyl glycerol sulfates, oleyl glycerol sulfates, alkyl phenol ether sulfates, primary paraffinsulfonates, alkylphosphates, alkyl ether phosphates, isethionates, such as acyl isethionates, N-acyltaurides, alkylsuccinamates, sulfosuccinates, monoesters of sulfosuccinates (particularly saturated and unsaturated $C_{12}$-$C_{18}$-monoesters) and diesters of sulfosuccinates (particularly saturated and unsaturated $C_{12}$-$C_{18}$-diesters), acylsarcosinates, sulfates of alkylpolysaccharides, such as sulfates of alkylglycosides, branched primary alkylsulfates and alkylpolyethoxycarboxylates, such as those of the formula $RO(CH_2CH_2)_kCH_2COOM$, in which R is a $C_8$-$C_{22}$-alkyl, k is a number from 0 to 10 and M is a cation which forms a soluble salt. Resin acids or hydrogenated resin acids, such as rosin or hydrogenated rosin or tall oil resins and tall oil resin acids can likewise be used. Further examples are described in "Surface Active Agents and Detergents" (Vol. I and II, Schwartz, Perry and Berch). A large number of such surfactants are also described in U.S. Pat. No. 3 929 678. Typical examples of anionic surfactants are also alkyl ether sulfonates, glycerol ether sulfonates, sulfo fatty acids, fatty alcohol ether sulfates, glycerol ether sulfates, hydroxy mixed ether sulfates, fatty acid amide (ether) sulfates, mono- and dialkylsulfosuccinates, mono- and dialkylsulfosuccinamates, sulfotriglycerides, amide soaps, alkyloligoglucosidesulfates, alkylamino sugar sulfates and alkyl (ether) phosphates. If the anionic surfactants contain polyglycol ether chains, they can have a conventional or a narrowed homolog distribution. In the compositions according to the invention it is possible to use nonionic surfactants, such as fatty acid alkyl ester alkoxylates, alkyl and/or alkenyl oligoglycosides, fatty alcohol polyglycol ethers, alkylphenol polyglycol ethers, fatty acid polyglycol esters, fatty acid amide polyglycol ethers, fatty amine polyglycol ethers, alkoxylated triglycerides, fatty acid glucamides, polyoil fatty acid esters, sugar esters, sorbitan esters and polysorbates and/or alkoxylated fatty alcohols. The proportion of nonionic surfactants overall relative to the total amount of all surfactants in the cleaners according to the invention is generally 1 to 50% by weight.

Furthermore, in the compositions according to the invention it is possible to use foam-enhancing cosurfactants from the group consisting of alkylbetaines, alkylamidobetaines, aminopropionates, aminoglycinates, imidazoliniumbetaines and sulfobetaines, amine oxides and fatty acid alkanolamides, particularly the monoethanolamides of palm kernal oil and coconut oil fatty acids or polyhydroxyamides in the amounts from 1 to 50% by weight.

The total amount of surface-active compounds can be up to 50% by weight, preferably 1 to 40% by weight, in particular 4 to 25% by weight, of the overall detergent or cleaner.

Suitable organic and inorganic builders are neutral or, in particular, alkaline salts which can precipitate out calcium ions or form complexes with them. Suitable and particularly ecologically acceptable builder substances are crystalline, layered silicates of the formula $NaMSi_{(x)}O_{(2x+1)}$, where M is sodium or hydrogen, x is a number from 1.9 to 22, preferably from 1.9 to 4 and y is a number from 0 to 33, for example Na SKS-5 ($\alpha$-$Na_2Si_2O_5$), Na SKS-7 ($\beta$-$Na_2Si_2O_5$, natrosilite), Na SKS- 9 ($NaHSi_2O_5$*$H_2O$), Na SKS-10 ($NaHSi_2O_3$*$3H_2O$, canemite), Na SKS-11 (t-$Na_2Si_2O_5$) and Na SKS-1 3 ($NaHSi_2O_5$), but in particular Na SKS- 6 ($\delta$-$Na_2Si_2O_5$), and finally crystalline synthetic hydrous zeolites, in particular of the type NaA, which have a calcium-binding capacity in the range from 100 to 200 mg of CaO/g. Zeolites and phyllosilicates can be present in the composition in an amount of up to 20% by weight. Also suitable are non-neutralized or partially neutralized (co) polymeric polycarboxylic acids. These include the homopolymers of acrylic acid or of methacrylic acid or copolymers thereof with further ethylenically unsaturated monomers, such as, for example, acrolein, dimethylacrylic acid, ethylacrylic acid, vinyl acetic acid, allyl acetic acid, maleic acid, fumaric acid, itaconic acid, (meth)allylsulfonic acid, vinylsulfonic acid, styrenesulfonic acid, acrylamidomethylpropanesulfonic acid, and monomers containing phosphorus groups, such as, for example, vinylphosphoric acid, allylphosphoric acid and acrylamidomethylpropanephosphoric acid and salts thereof, and hydroxyethyl(meth) acrylate sulfate, allyl alcohol sulfate and allyl alcohol phosphates.

Preferred (co)polymers have a mean molar mass from 1000 to 100,000 g/mol, preferably from 2000 to 75,000 g/mol and in particular from 2000 to 35,000 g/mol. The degree of neutralization of the acid groups is advantageously 0 to 90%, preferably 10 to 80% and in particular 30 to 70%.

Suitable polymers include, in particular, homopolymers of acrylic acid and copolymers of (meth)acrylic acid with maleic acid or maleic anhydride.

Further suitable copolymers are derived from terpolymers which can be obtained by polymerizing from 10 to 70% by weight of monoethylenically unsaturated dicarboxylic acids having 4 to 8 carbon atoms, salts thereof, 20 to 85% by weight of monoethylenically unsaturated monocarboxylic acids having 3 to 10 carbon atoms or salts thereof, 1 to 50% by weight of monounsaturated monomers which, following hydrolysis, release hydroxyl groups at the polymer chain, and 0 to 10% by weight of further, free-radically copolymerizable monomers.

Likewise suitable are graft polymers of monosaccharides, oligosaccharides, polysaccharides and modified polysaccharides, and animal or vegetable proteins. Preference is given to copolymers of sugar and other polyhydroxy compounds and a monomer mixture of 45 to 96% by weight of monoethylenically unsaturated $C_3$- to $C_{10}$-monocarboxylic acids or mixtures of $C_3$- to $C_{10}$-monocarboxylic acids and/or salts thereof containing monovalent cations, 4 to 55% by weight of monomers containing monoethylenically unsaturated monosulfonic acid groups, monoethylenically unsaturated sulfuric esters, vinylphosphoric esters and/or the salts of these acids containing monovalent cations, and 0 to 30% by weight of water-soluble unsaturated compounds which have been modified with 2 to 50 mol of alkylene oxide per mol of monoethylenically unsaturated compounds.

Further suitable polymers are polyaspartic acid or derivatives thereof in non-neutralized or only partially neutralized form. Particularly suitable are also graft polymers of acrylic acid, methacrylic acid, maleic acid and further ethylenically unsaturated monomers to salts of polyaspartic acid, as are customarily produced during the above-described hydrolysis of polysuccinimide. In this connection, it is possible to dispense with the otherwise necessary addition of acid for the preparation of the only partially neutralized form of polyaspartic acid. The amount of polyaspartate is usually chosen such that the degree of neutralization of all of the carboxyl groups incorporated in the polymer does not exceed 80%, preferably 60%.

Further builders which can be used are, for example, the percarboxylic acids, preferably used in the form of their sodium salts, such as citric acid, in particular trisodium citrate and trisodium citrate dihydrate, nitrilotriacetic acid and its water-soluble salts; alkali metal salts of carboxymethyloxysuccinic acid, ethylenediaminetetraacetic acid, mono-, dihydroxysuccinic acid, $\alpha$-hydroxypropionic acid, gluconic acid, mellitic acid, benzopolycarboxylic acids and [lacuna] as disclosed in U.S. Pat. No. 4,144,226 and 4,146,495. Phosphate-containing builders, for example alkali metal phosphates, which can be in the form of their alkaline, neutral or acidic sodium or potassium salts, are also suitable. Examples thereof are trisodium phosphate, tetrasodium diphosphate, disodium dihydrogenphosphate, pentasodium triphosphate, so-called sodium hexametaphosphate, oligomeric trisodium phosphate with amounts of oligomerization in the range from 5 to 1000, in particular 5 to 50, and mixtures of sodium and potassium salts. The builder substances can be present in amounts of from 5% by weight to 80% by weight, preference being given to a proportion of from 10% by weight to 60% by weight.

The desired viscosity of the compositions can be adjusted by adding water and/or organic solvents or by adding a combination of organic solvents and thickeners.

In principle, suitable organic solvents are all mono- or polyhydric alcohols. Preference is given to using alcohols having 1 to 4 carbon atoms, such as methanol, ethanol, propanol, isopropanol, straight-chain and branched butanol, glycerol and mixtures of said alcohols. Further preferred alcohols are polyethylene glycols having a relative molecular mass below 2000. In particular, the use of polyethylene glycol having a relative molecular mass between 200 and 600 and in amounts of up to 45% by weight, and of polyethylene glycol having a relative molecular mass between 400 and 600 in amounts of from 5 to 25% by weight is preferred. An advantageous mixture of solvents consists of monomeric alcohol, for example ethanol and polyethylene glycol in the ratio 0.5:1 to 1.2:1.

Further suitable solvents are, for example, triacetin (glycerol triacetate) and 1-methoxy-2-propanol.

The thickeners used are preferably hydrogenated castor oil, salts of long-chain fatty acids, which [lacuna] preferably in amounts of from 0 to 5% by weight and in particular in amounts of from 0.5 to 2% by weight, for example sodium, potassium, aluminum, magnesium and titanium stearates or the sodium and/or potassium salts of behenic acid, and polysaccharides, in particular xanthan gum, guar guar, agar agar, alginates and Tyloses, carboxymethylcellulose and hydroxyethylcellulose, and also higher molecular weight polyethylene glycol mono- and diesters of fatty acids, polyacrylates, polyvinyl alcohol and polyvinylpyrrolidone, and electrolytes such as sodium chloride and ammonium chloride. Suitable thickeners are water-soluble polyacrylates which have, for example, been crosslinked with approximately 1 % of a polyallyl ether of sucrose, and which have a relative molecular mass above one million. Examples thereof are the polymers obtainable under the name Carbopol® 940 and 941. The crosslinked polyacrylates are used in amounts not exceeding 1% by weight, preferably in amounts of from 0.2 to 0.7% by weight.

Suitable enzymes are those from the class of proteases, such as BLAP, Optimase, Opticlean, Maxacal, Maxapem, Esperase, Savinase, Purifect OxP and/or Durazym, lipases, such as Lipolase, Lipomax, Lumafast and/or Lipozym, amylases, such as Termamyl, Ainylase-LT, Maxamyl, Duramyl and/or Purafect OxAm, and cutinases, pullulanases and mixtures thereof. Their proportion can be from 0.2 to 1% by weight. The enzymes can be adsorbed to carrier substances and/or embedded in coating substances.

Possible silver corrosion inhibitors are the compounds given in DE 196 49 375.

As foam regulators, it is possible to add, preferably, up to 6% by weight, in particular about 0.5% by weight to 4% by weight, of foam-suppressing compounds, preferably from the group of silicone oils, mixtures of silicone oil and hydrophobicized silica, paraffins, paraffin/alcohol combinations, hydrophobicized silica, bis-fatty acid amides and other known commercially available antifoams.

To set a desired pH which does not result by mixing the other components by itself, the compositions according to the invention can comprise system- and environmentally-compatible acids, in particular citric acid, acetic acid, tartaric acid, malic acid, lactic acid, glycolic acid, succinic acid, glutaric acid and/or adipic acid, or else mineral acids, in particular sulfuric acid or alkali metal hydrogensulfates or bases, in particular ammonium or alkali metal hydroxides. Such pH regulators are present in the compositions according to the invention in amounts which, preferably, do not exceed 10% by weight, in particular in amounts of from 0.5% by weight to 6% by weight.

Examples of suitable preservatives are phenoxyethanol, formaldehyde solution, pentanediol or sorbic acid. Suitable pearlizing agents are, for example, glycol distearic esters, such as ethylene glycol distearate, but also fatty acid monoglycol esters. Suitable salts or extenders are, for example, sodium sulfate, sodium carbonate or sodium silicate (water glass).

Typical individual examples of further additives which can be mentioned are sodium borate, starch, sucrose, polydextrose, RAED, stilbene compounds, methylcellulose, toluene sulfonate, cumene sulfonate, soaps and silicones.

The bleaching catalysts of this invention can be used in a large number of products. These include textile detergents, textile bleaches, surface cleaners, toilet cleaners, dishwasher detergents and also denture cleaners. The detergents can be in solid or liquid form.

For reasons of stability and handlability, it is advantageous to use the bleach activators in the form of granules which, in addition to the bleaching catalyst, comprise a binder. Various methods of preparing such granules are described in the patent literature, for example in Canadian Patent No. 1102966, GB 1561333, U.S. Pat. No. 4087369, EP 240057, EP 241962, EP 101634 and EP 62523. The granules which comprise the bleaching catalyst according to the invention are generally added to the detergent composition together with the other dry constituents, such as, for example, enzymes, inorganic peroxide bleaches. The detergent composition to which the catalyst granules are added can be obtained in a variety of ways, such as, for example, mixing the dry components, extruding or spray-drying.

In a further embodiment, the bleaching catalysts according to the invention are particularly suitable for non-aqueous liquid detergents, together with a bleaching peroxide compound as described in EP-0 869 171. These are compositions in the form of a non-aqueous liquid medium in which a solid phase can be dispersed. The non-aqueous liquid medium can be a liquid, surface-active substance, preferably a nonionic surface-active substance, a nonpolar liquid medium, such as, for example, liquid paraffin, a polar solvent, such as, for example, polyols, for example glycerol, sorbitol, ethylene glycol, possibly in conjunction with low molecular weight monohydric alcohols, such as ethanol or isopropanol or mixtures thereof.

The solid phase can consist of builder substances, alkalis, abrasive substances, polymers and solid ionic surface-active compounds, bleaches, fluorescent substances and other customary solid ingredients.

The examples below serve to illustrate the invention in more detail without limiting it thereto.

EXAMPLES

Example 1

Preparation of 2,6-bis(4,7-dimethyl-1,4,7-triazacyclonon-1-ylmethyl)4-methylphenol (dtmp)

At 0° C., 3.26 g (16 mmol) of 2,6-bischloromethyl4-methylphenol are added in portions to a solution of 5 g (32 mmol) of 1,4-dimethyl-1,4,7-triazacyclononane and 3.21 g (32 mmol) of triethylamine in 150 ml of methanol, and the mixture is stirred for 4 days at room temperature. For work-up, 1.28 g (32 mmol) of sodium hydroxide are added, and the sodium chloride which forms is filtered off. The solvent is removed under reduced pressure and the product is dried for one day under a high vacuum. Yield: 6.1 g (86%). Analysis: $^1$H-NMR:$\delta$=2.24 (s,3 H, $C_{arom.}$—$CH_3$); 2.35 (s,12 H, N-$CH_3$); 2.64 (m, 8 H, $C_{arom.}$—$CH_2$—N—$CH_2$—$CH_2$—N); 2.67 (s, 8 H, $H_3$C—N—$CH_2$—$CH_2$—N—$CH_3$); 2.87 (m, 8 H, $C_{arom.}$—$CH_2$N—$CH_2$—$CH_2$—N); 3.73 (s, 4 H, $C_{arom.}$—$CH_2$N); 6.82 (s, 2 H, $C_{arom.}$—H) $^{13}$C-NMR: $\delta$=20.4 ($C_{arom.}$—$CH_3$); 45.4 (N—$CH_3$); 53.0; 55.9; 56.2; (N—$CH_2$—$CH_2$—N); 58.6 ($C_{arom.}$—$CH_2$—N); 123.0 ($C_{arom.}$—$CH_2$—N); 127.4 ($C_{arom.}$—$CH_3$); 130.0 ($C_{arom.}$—H), 154.7 ($C_{arom.}$—OH) MS: (electrospray) m/e=447 (M+H⊕, 100%)

Example 2

Preparation of dimanganese $\mu$-[2,6-bis(4,7-dimethyl-1,4,7-triazacyclonon-1-ylmethyl)4-methylphenolato]-bis($\mu$-acetato) hexafluorophosphate (manganese complex I )

6 g (13.4 mmol) of 2,6-bis(4,7-dimethyl-1,4,7-triazacyclonon-1-ylmethyl)-4-methylphenol are dissolved in 150 ml of methanol, and, over the course of 30 min, 6.6 g (27 mmol) of manganese(ll) acetate 4 H$_2$O and 2.4 g (13.5 mmol) of KPF$_6$ are added alternately in equal portions. After the mixture has been stirred for one day at room temperature, the complex is precipitated out with water, then filtered off under reduced pressure and washed with aqueous methanol, and the resulting green solid is dried for two days under reduced pressure. Yield: 9.9 g (91%). Analysis: MS: electrospray m/e=673 (M-PF$_6^-$, 100%), FAB m/e=673 (M-PF$_6^-$,100%)

| Elemental analysis: | %N (found) 10.11 | %N (calc.) 10.24 |
|---|---|---|
| | %C (found) 42.27 | %C (calc.) 42.45 |
| | %H (found) 6.33 | %H (calc.) 6.51 |

The structure of the complex was also verified by X-ray structural analysis, cyclovoltametry and magnetization measurement. The compound crystallizes in the monoclinic space group P 2/c where a=17.5505(10)Å, b=10.3361(2)Å, c=20.4256(5)Å, β=93.115(10)° and Z=4. The structure contains positively charged bicyclic cations separated by the hexafluorophosphate anion. The manganese ions are bridged by two bidentate acetate groups and the central phenoxy oxygen of the heptadentate ligands. Three N-donor atoms form the arms of the ligand, which facially coordinates each Mn atom and completes the N$_3$O$_3$ coordination. The cyclovoltametry shows two reversible oxidation signals at 14 mV and 528 mV vs. ferrocene/ferrocinium. The temperature-dependent magnetization measurement at 1 T gives a S$_{tot}$= ground state and an antiferromagnetic temperature behavior. The effective magnetic moment is 1.6 μB at 2K and increases steadily to 7.15 μB. Refinement gave a magnetic exchange interaction of J=−4.3 cm$^{-1}$.

Example 3

Preparation of 2,6-bis(4,7-dimethyl-1,4,7-triazacyclonon-1-ylmethyl)-4-methylanisole (dtma)

0.31 g (1 mmol) of 2,6-bis bromomethyl-4-methylanisole are added over the course of 30 min to a solution of 0.31 g (2 mmol) of 1,4-dimethyl-1,4,7-triazacyclononane, 0.14 g of K$_2$CO$_3$ (1 mmol) in 10 ml of toluene, and the reaction mixture is refluxed under a protective gas for 2 days.

After the mixture had been cooled to room temperature, the precipitated KBr was filtered off over Celite, and then the solvent was distilled off under reduced pressure. The yellowish oil which remains is freed from residual toluene under a high vacuum and requires no further purification. Yield: 0.39 g (85%).

Analysis: $^1$H-NMR:δ=2.31 (s, 3 H, C$_{arom.}$—CH$_3$); 2.35 (s, 12 H, N—CH$_3$); 2.71 (m, 16 H, —CH$_2$—N—CH$_2$—CH$_2$—N—CH$_2$—); 2.93 (s, 8 H, H$_3$C—N—CH$_2$—CH$_2$—N—CH$_3$); 3.68 (s, 4 H, C$_{arom.}$—CH$_2$N); 7.17 (s, 2 H, C$_{arom.}$—H) $^{13}$C-NMR:δ=21.0 (C$_{arom.}$—CH$_3$); 46.5 (N—CH$_3$); 55.8; 56.3; 57.0; 57.2 (OCH$_3$; N—CH$_2$—CH$_2$—N); 61.4 (C$_{arom.}$—CH$_2$—N); 130.3 (C$_{arom.}$—H); 132.4 (C$_{arom.}$—CH$_2$—N); 132.6 (C$_{arom.}$—CH$_3$); 155.1 (C$_{arom.}$—OCH$_3$) MS: (electrospray) m/e=460 (M+H⊕, 100%)

Example 4

Preparation of dimanganese μ-[2,6-bis(4,7-dimethyl-1,4,7-triazacyclonon-1-ylmethyl)-4-methylanisole]-μ-oxo-bis(μ-acetato)-dihexafluorophosphate (manganese complex II)

0.16 g (0.6 mmol) of manganese(II) acetate trihydrate are added to 0.14 g (0.3 mmol) of bcmmp, 0.12 g (1.5 mmol) of sodium acetate and 0.28 g (1.5 mmol) of KPF$_6$ dissolved in 30 ml of methanol. After the mixture has been stirred for one day, the red solid is filtered off under reduced pressure, washed with methanol and dried for two days under reduced pressure. 0.25 g (85%) of a red-violet solid were obtained. Analysis: MS (electrospray): m/e=849 (M-PF$_6^-$, 100%)

| Elemental analysis: | %N (found) 8.27 | %N (calc.) 8.45 |
|---|---|---|
| | %C (found) 35.86 | %C (calc.) 36.23 |
| | %H (found) 5.21 | %H (calc.) 5.49 |

The structure of the complex was also confirmed by UV-VIS, IR, spectroelectrochemistry, magnetization measurement and EPR.

The UV-VIS spectra have the expected bands, the bands at 487 and 521 nm and the associated absorbances are characteristic of the chromophore Mn$^{III}$—O—Mn$^{III}$:

Band/[nm] (ε/[lmol$^{-1}$cm$^{-1}$] 245 (5500), 283 (6200), 307 (6000), 487 (390), 521 (370), 704 (100). In the IR, the antisymmetric oscillation of the bridging oxygen is at 742 cm$^{-1}$. The complex is EPR-silent. The spectroelectrochemistry documents the possibility of chemically reversible oxidation of the Mn$^{III}$Mn$^{III}$ species to the Mn$^{III}$Mn$^{IV}$ and Mn$^{III}$Mn$^{II}$ forms and the characteristic change in the band positions and absorbances. The associated EPR spectra indicate the heterovalency of the species produced from the Mn$^{III}$Mn$^{III}$ complex. Thus, the Mn$^{III}$Mn$^{IV}$ species in the X-band shows the expected well-resolved 16-line spectrum around g=2. The magnetization measurement shows the weak ferromagnetic coupling where J=5.3 cm$^{-1}$. Bleaching test A bleach formulation A was prepared by mixing 200 ml of an aqueous solution of the reference detergent WMP from Waschereiforschung Krefeld [Krefeld Laundry Research] (concentration 2 g/l of WMP in water with 15° German hardness) with 200 mg of sodium percarbonate and 2 mg of the respective catalyst. A further formulation B is obtained by the additional addition of 100 mg of tetraacetylethylenediamine (TAED). Using these formulations, bleach-sensitive standard test fabric from Watschereiforschung Krefeld [Krefeld Laundry Research] (WFK) soiled with tea (BC-1) and curry (BC-4) were subjected to a treatment at a temperature of 40° C. under isothermal washing conditions in a Linitest apparatus (Heraeus). After a washing time of three minutes, the swatches of fabric were rinsed with water, dried and ironed. The bleaching effect was then quantified by determining the difference ΔR(formulation+catalyst) in reflectances before and after the washing operation using a whiteness measuring instrument (ELREPHO 2000, Datacolor). From these ΔR(formulation+catalyst) values and the ΔR(formulation) values determined in control experiments without bleaching catalyst were calculated the ΔΔR values listed in Table 1, which is a direct measure of the improvement in the bleaching action as a result of the addition of catalyst:

ΔΔR=ΔR(formulation+catalyst)-ΔR(formulation)

TABLE 1

Average values of the differences in reflectance ΔΔR from three determinations in each case

| Bleach formulation | Catalyst | Tea BC-1 | Curry BC-4 |
|---|---|---|---|
| A | Manganese complex I | 7.6 | 10.0 |
| B | Manganese complex I | 6.0 | 8.3 |

TABLE 1-continued

Average values of the differences in reflectance ΔΔR from three determinations in each case

| Bleach formulation | Catalyst | Tea BC-1 | Curry BC-4 |
|---|---|---|---|
| A | Manganese complex II | 8.2 | 8.7 |
| B | Manganese complex II | 4.5 | 7.0 |

Further advantageous properties of the complexes described are low color damage and low fiber damage.

What is claimed is:

1. A compound of the general formula I

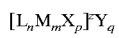     formula I where

M is manganese in oxidation state II, III, IV and/or V, iron in oxidation state II and/or IIII or cobalt in oxidation state II and/or III, X is a coordination group or bridging group, Y is a counterion in the corresponding stoichiometric amount to balance an existing charge z, where z as the charge of the metal complex can be positive, zero or negative, n and m, independently of one another, are integers from 1 to 4, p is an integer from 0 to 15, q is z/charge of Y, L is an organic ligand of the general formula II

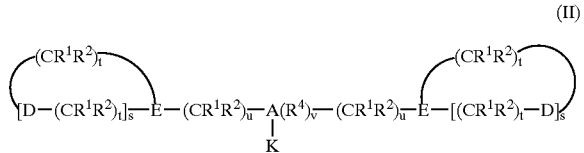 (II)

where $R^1$ and $R^2$, independently of one another, are hydrogen, an alkyl group having 1 to 6 carbon atoms, an alkoxy group having 1 to 3 carbon atoms, an alkenyl or alkinyl group having 2 to 8 carbon atoms, a cycloalkyl group having 3 to 10 carbon atoms or a phenyl group which may also be substituted, each D, independently of one another, is $NR^3$, O, $PR^3$ or S, where $R^3$ is an alkyl group having 1 to 6 carbon atoms, an alkenyl or alkinyl group having 2 to 8 carbon atoms, a cycloalkyl group having 3 to 10 carbon atoms or a phenyl group which may also be substituted, each E, independently of one another, is N, P or $C(R^1)$ with the meanings given above for $R^1$, t is a number from 0 to 6, s is a number from 1 to 5 and u is a number from 1 to 4, A is a $C_3$- to $C_9$-cycloalkyl, phenyl, 1,1'-biphenyl, naphthyl, anthracenyl or pyridinyl radical, each $R^4$, independently of one another, is hydrogen, a $C_1$- to $C_6$-alkyl group, a $C_1$- to $C_3$-alkoxy group, a $C_3$- to $C_1 0$-cycloalkyl group or a phenyl group which may also be substituted, v is a number from 0 to 15, K is a group coordinating to at least one of the metal centers M and is of the type —O, —OR, —S, —SR, —$NR_2$, —NR, —$PR_2$ or —PR, where R is hydrogen, an alkyl group having 1 to 6 carbon atoms, an alkenyl or alkinyl group having 2 to 8 carbon atoms, a cycloalkyl group having 3 to 10 carbon atoms or a phenyl group which may also be substituted, X is an anion of the following formulae:

$F^-$, $Cl^-$, $Br^-$, $SCN^-$, $OH^-$, $O_2^{2-}$, $O_2^-$, $R^{10}OO^-$, $H_2O$, $HS^-$, $CN^-$, $OCN^-$, $S^{2-}$, $N_3^-$, $NH_3$, $NR^{10}_3$, $NR^0_2^-$, $R^{10}O^-$, $R^{10}COO^-$, $R^{10}_3^-$ and $R^{10}SO_4^-$, where $R^{10}$ is in each case hydrogen, $C_1$- to $C_8$-alkyl, $C_3$- to $C_8$-cycloalkyl or $C_6$- to $C_{18}$-aryl, and

Y if z is positive, is an anion of the following formulae: $F^-$, $Cl^-$, $Br^-$, $NO_3^-$, $ClO_4^-$, $SCN^-$, $PF_6^-$, $R^{10}SO_4^-$, $R^{10}COO^-$, $R^{10}SO_3^-$, $BF_4^-$, $BPh_4^-$ and $SO_4^{2-}$ and if z is negative, is a cation of the following formulae: $Li^+$, $Na^+$, $K^+$, $Mg^{2+}$, $Ca^{2+}$, $Al^{3+}$, $NH_4^+$, $R^{10}NH_3^+$, $R^{10}_2NH_2^+$, $R^{10}_3NH^+$ and $R^{10}_4N^+$, where $R^{10}$ has the meaning given above.

2. A compound of the formula I as claimed in claim 1, wherein D is $NR^3$, E is nitrogen, $R^1$ and $R^2$ are hydrogen, s is a number from 1 to 3, t is a number from 1 to 4 and K is a group of the type —O, —OR, —S or —$NR_2$, and the other symbols have the meanings given in claim 1.

3. A compound of the formula I as claimed in claim 1, wherein D is $NR^3$, E is nitrogen, $R^1$ and $R^2$ are hydrogen, s is a number from 1 to 3, t is a number from I to 4, A is a phenyl or $C_3$-Cg-cycloalkyl group, m is a number from 1 to 3, n is a number from 1 to 2 and K is a group of the type —O, —OR, —S or —$NR_2$, and the other symbols have the meanings given in claim 1.

4. A compound of the formula I as claimed in claim 1, wherein the ligand L is 2,6-bis(4,7-dimethyl-1,4,7-triazacyclonon-1-ylmethyl)4-methylphenoxide.

5. A compound of the formula I as claimed in claim 1, wherein the ligand L is 2,6-bis(4,7-dimethyl-1,4,7-triazacyclonon-1-ylmethyl)-4-methylanisole.

6. A compound of the formula I as claimed in claim 1, wherein the transition metal M is manganese.

7. A process for bleaching textile or paper substrate comprising contacting said substrate with an aqueous liquor comprising the compound of claim 1 wherein $NR^3$ under the definition of D further comprises NH, and A further comprises carbon.

8. A process for washing dishes comprising contacting the dishes with detergent formulations or dishwashing detergents which comprise the compound of claim 1, wherein $NR^3$ under the definition of D further comprises NH, and A further comprises carbon.

* * * * *